(12) United States Patent
Gao et al.

(10) Patent No.: US 10,031,074 B2
(45) Date of Patent: Jul. 24, 2018

(54) SYSTEMS AND METHODS OF CALIBRATING INTEGRATED COMPUTATIONAL ELEMENTS

(71) Applicant: Halliburton Energy Services, Inc., Houston, TX (US)

(72) Inventors: Li Gao, Katy, TX (US); David L. Perkins, The Woodlands, TX (US); Michael T. Pelletier, Houston, TX (US); Dingding Chen, Tomball, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 1028 days.

(21) Appl. No.: 14/362,551

(22) PCT Filed: Sep. 25, 2013

(86) PCT No.: PCT/US2013/061574
§ 371 (c)(1),
(2) Date: Jun. 3, 2014

(87) PCT Pub. No.: WO2015/047238
PCT Pub. Date: Apr. 2, 2015

(65) Prior Publication Data
US 2015/0300945 A1    Oct. 22, 2015

(51) Int. Cl.
*G01N 21/27* (2006.01)
*G01N 33/28* (2006.01)
*G01N 21/31* (2006.01)

(52) U.S. Cl.
CPC ......... *G01N 21/274* (2013.01); *G01N 21/314* (2013.01); *G01N 33/2841* (2013.01); *G01N 2021/3174* (2013.01)

(58) Field of Classification Search
CPC ............... G01N 21/274; G01N 21/314; G01N 21/3174; G01N 33/2841; G01N 2021/3174
See application file for complete search history.

(56) References Cited

U.S. PATENT DOCUMENTS 5,691,809 A * 11/1997 Tackett .................. G01N 21/64
356/72
5,748,308 A * 5/1998 Lindberg .................. G01J 3/02
356/243.1

(Continued)

FOREIGN PATENT DOCUMENTS

EP          2400278       * 12/2011
WO     2015047238 A1      4/2015

OTHER PUBLICATIONS

International Search Report and Written Opinion for PCT/US2013/061574 dated May 9, 2014.

*Primary Examiner* — Mohamed Charioui
*Assistant Examiner* — Catherine Rastovski
(74) *Attorney, Agent, or Firm* — McDermott Will & Emery LLP

(57) ABSTRACT

Disclosed are systems and methods for calibrating integrated computational elements. One method includes measuring with a spectrometer sample interacted light comprising spectral data derived from one or more calibration fluids at one or more calibration conditions, the one or more calibration fluids circulating in a measurement system, programming a virtual light source based on the spectral data, simulating the spectral data with the virtual light source and thereby generating simulated fluid spectra corresponding to the spectral data, conveying the simulated fluid spectra to the one or more ICE and thereby generating corresponding (Continued)

beams of optically interacted light, and calibrating the one or more ICE based on the corresponding beams of optically interacted light.

20 Claims, 3 Drawing Sheets

(56) References Cited

U.S. PATENT DOCUMENTS

| | | | |
|---|---|---|---|
| 7,899,636 B2 | 3/2011 | Bakker | |
| 8,212,216 B2 | 7/2012 | Perkins et al. | |
| 8,237,920 B2 | 8/2012 | Jones et al. | |
| 8,345,234 B2 | 1/2013 | Myrick et al. | |
| 8,352,205 B2 | 1/2013 | Myrick et al. | |
| 2008/0094623 A1 | 4/2008 | Schuurmans et al. | |
| 2009/0316150 A1* | 12/2009 | Myrick | G01J 3/02 356/326 |
| 2010/0265509 A1* | 10/2010 | Jones | E21B 47/102 356/445 |
| 2012/0127466 A1* | 5/2012 | Karnes | G01N 11/04 356/319 |
| 2012/0170023 A1* | 7/2012 | Szobota | G01N 21/552 356/51 |
| 2016/0178511 A1* | 6/2016 | Gao | G01N 33/2823 250/267 |

* cited by examiner

SYSTEMS AND METHODS OF CALIBRATING INTEGRATED COMPUTATIONAL ELEMENTS

BACKGROUND

The present disclosure relates to optical computing devices that employ integrated computational elements and, more particularly, to improved systems and methods for calibrating integrated computational elements.

Optical computing devices, also commonly referred to as "opticoanalytical devices," can be used to analyze and monitor a substance in real time. Such optical computing devices will often employ an optical processing element that optically interacts with the substance or a sample thereof to determine quantitative and/or qualitative values of one or more physical or chemical properties of the substance. The optical element may be, for example, an integrated computational element (ICE), also known as a multivariate optical element (MOE), which is essentially an optical interference filter that can be designed to operate over a continuum of wavelengths in the electromagnetic spectrum from the UV to mid-infrared (MIR) ranges, or any sub-set of that region. Electromagnetic radiation that optically interacts with a substance is changed and filtered by the ICE so as to be readable by a detector, such that an output of the detector can be correlated to the physical or chemical property of the substance being analyzed.

An ICE (hereafter "ICE component") typically includes a plurality of optical layers consisting of various materials whose index of refraction and size (e.g., thickness) may vary between each layer. An ICE design refers to the number and thickness of the respective layers of the ICE component. The layers may be strategically deposited and sized so as to selectively pass predetermined fractions of electromagnetic radiation at different wavelengths configured to substantially mimic a regression vector corresponding to a particular physical or chemical property of interest of a substance. Accordingly, an ICE design will exhibit a transmission function that is weighted with respect to wavelength. As a result, the output light intensity from the ICE component conveyed to the detector may be related to the physical or chemical property of interest for the substance.

After manufacture and before it is put into field use, each ICE component must be carefully calibrated against known calibration fluids for all temperature and pressure ranges expected to be encountered in the field. This calibration process, however, can be quite complicated and time consuming. For instance, the time required to calibrate an ICE component is multiplied by the number of calibration fluids used in the calibration system. In an example system that employs ICE to measure reservoir fluids downhole, there are typically five calibration fluids used, but this number can increase depending on time and required accuracy. The time required to calibrate an ICE component is also multiplied by the number of gas charges (for gas-to-oil ratio) applied to each calibration fluid. For instance, gas-oil-ratio (GOR) calibration requires gas charging stages that entail long set-up times in order to ensure uniform mixing between the calibration fluid in the calibration system and any newly added gas volumes.

Lastly, the time required to calibrate an ICE component is also multiplied by the number of desired temperature and pressure data points used. At each desired temperature and pressure data point, there is a lengthy delay before the temperature and pressure control systems are able to equilibrate the calibration fluid to a steady state before data can be obtained. All of these requirements can result in weeks of continuously running the calibration routine in order to calibrate a single set of ICE components for field operations.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
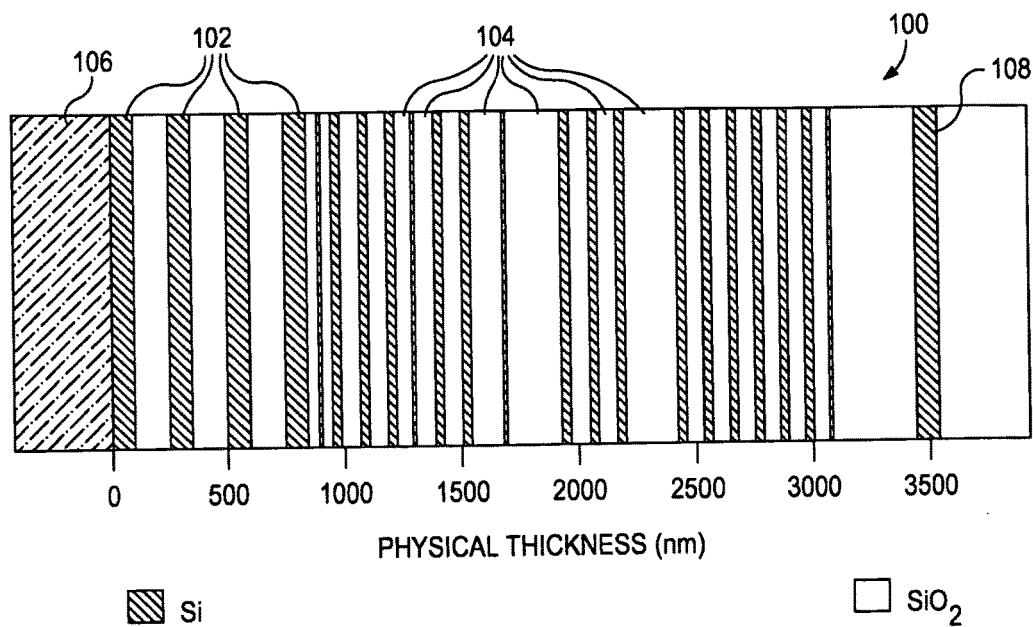
FIG. 1 illustrates an exemplary integrated computation element, according to one or more embodiments.

The present disclosure relates to optical computing devices that employ integrated computational elements and, more particularly, to improved systems and methods for calibrating integrated computational elements.

The present disclosure provides improved systems and methods for calibrating integrated computational elements (ICE) for use in optical computing devices. The improved calibration methods replace the current brute force calibration procedure for ICE components by using an agile light source containing all the required spectral responses for all calibration fluids, at all desired temperature, pressure and gas-oil-ratio (GOR) points. Advantageously, and as will be described in greater detail below, only a single set of complete laboratory data is required after which subsequent calibrations can be carried out "virtually" without any actual laboratory time. As a result, the time required to properly calibrate an ICE component can be reduced from weeks to hours. Such improved calibration technique may contribute to substantial capital expenditure savings since no complex pressure-volume-temperature (PVT) lab equipment is needed after the first complete laboratory data is obtained. Consequently, the improved systems and methods described herein may be easily adaptable for field calibration where PVT equipment is not readily available.

The disclosed systems and methods may be suitable for calibrating ICE components for use in the oil and gas industry. It will be appreciated, however, that the various disclosed systems and methods are equally applicable to calibrating ICE components for use in other technology fields including, but not limited to, the food and drug industry, industrial applications, mining industries, or any field where it may be advantageous to determine in real-time or near real-time a characteristic of a specific substance.

As used herein, the term "characteristic" refers to a chemical, mechanical, or physical property of a substance. The characteristic of a substance may include a quantitative or qualitative value of one or more chemical constituents or compounds present therein or any physical property associated therewith. Such chemical constituents and compounds may be referred to herein as "analytes." Illustrative characteristics of a substance that can be detected with the ICE components described herein can include, for example, chemical composition (e.g., identity and concentration in total or of individual components), phase presence (e.g., gas, oil, water, etc.), impurity content, pH, alkalinity, viscosity, density, ionic strength, total dissolved solids, salt content (e.g., salinity), porosity, opacity, bacteria content, total hardness, combinations thereof, state of matter (solid, liquid, gas, emulsion, mixtures, etc.), and the like.

As used herein, the term "substance," or variations thereof, refers to at least a portion of matter or material of interest to be tested or otherwise evaluated using the optical computing devices described herein. The substance includes the characteristic of interest, as defined above. The substance may be any fluid capable of flowing, including particulate solids, liquids, gases (e.g., air, nitrogen, carbon dioxide, argon, helium, methane, ethane, butane, and other hydrocarbon gases, hydrogen sulfide, and combinations thereof), slurries, emulsions, powders, muds, glasses, mixtures, combinations thereof, and may include, but is not limited to, aqueous fluids (e.g., water, brines, etc.), non-aqueous fluids (e.g., organic compounds, hydrocarbons, oil, a refined component of oil, petrochemical products, and the like), acids, surfactants, biocides, bleaches, corrosion inhibitors, foamers and foaming agents, breakers, scavengers, stabilizers, clarifiers, detergents, a treatment fluid, fracturing fluid, a formation fluid, or any oilfield fluid, chemical, or substance as found in the oil and gas industry. The substance may also refer to a solid material such as, but not limited to, rock formations, concrete, solid wellbore surfaces, and solid surfaces of any wellbore tool or projectile (e.g., balls, darts, plugs, etc.).

As used herein, the term "electromagnetic radiation" refers to radio waves, microwave radiation, terahertz, infrared and near-infrared radiation, visible light, ultraviolet light, X-ray radiation and gamma ray radiation.

As used herein, the term "optical computing device" refers to an optical device that is configured to receive an input of electromagnetic radiation interacted with a substance and produce an output of electromagnetic radiation from a processing element arranged within or otherwise forming part of the optical computing device. The processing element may be, for example, an integrated computational element (ICE), also known as a multivariate optical element (MOE). The electromagnetic radiation that optically interacts with the processing element is changed so as to be readable by a detector, such that an output of the detector can be correlated to a particular characteristic of the substance. The output of electromagnetic radiation from the processing element can be reflected, transmitted, and/or dispersed electromagnetic radiation. Whether the detector analyzes reflected, transmitted, or dispersed electromagnetic radiation may be dictated by the structural parameters of the optical computing device as well as other considerations known to those skilled in the art. In addition, emission and/or scattering of the substance, for example via fluorescence, luminescence, Raman, Mie, and/or Raleigh scattering, can also be monitored by optical computing devices.

As used herein, the term "optically interact" or variations thereof refers to the reflection, transmission, scattering, diffraction, or absorption of electromagnetic radiation either on, through, or from one or more processing elements (i.e., ICE or MOE components), a substance being analyzed by the processing elements, or a polarizer used in an optical computing device. Accordingly, optically interacted light refers to electromagnetic radiation that has been reflected, transmitted, scattered, diffracted, or absorbed by, emitted, or re-radiated, for example, using a processing element, but may also apply to optical interaction with a substance or a polarizer.

As mentioned above, the processing element used in the above-defined optical computing devices may be an ICE component. In operation, an ICE component is capable of distinguishing electromagnetic radiation related to a characteristic of interest of a substance from electromagnetic radiation related to other components of the substance. Referring to FIG. 1, illustrated is an exemplary ICE 100, according to one or more embodiments of the present disclosure. As illustrated, the ICE 100 may include a plurality of alternating layers 102 and 104, such as silicon (Si) and SiO$_2$ (quartz), respectively. In general, these layers 102, 104 consist of materials whose index of refraction is high and low, respectively. Other examples of materials might include niobia and niobium, germanium and germania, MgF, SiO, and other high and low index materials known in the art. The layers 102, 104 may be strategically deposited on an optical substrate 106. In some embodiments, the optical substrate 106 is BK-7 optical glass. In other embodiments, the optical substrate 106 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the optical substrate 106 in FIG. 1), the ICE 100 may include a layer 108 that is generally exposed to the environment of the device or installation, and may be able to detect a sample substance. Layer 108 may or may not be birefringent. The number of layers 102, 104 and the thickness of each layer 102, 104 are determined from the spectral attributes acquired from a spectroscopic analysis of a characteristic of the substance being analyzed using a conventional spectroscopic instrument. The spectrum of interest of a given characteristic typically includes any number of different wavelengths.

It should be understood that the exemplary ICE 100 in FIG. 1 does not in fact represent any particular ICE component configured to detect a specific characteristic of a given substance, but is provided for purposes of illustration only. Consequently, the number of layers 102, 104 and their relative thicknesses, as shown in FIG. 1, bear no correlation to any particular substance or characteristic thereof. Nor are the layers 102, 104 and their relative thicknesses necessarily drawn to scale, and therefore should not be considered limiting of the present disclosure.

In some embodiments, the material of each layer 102, 104 can be doped or two or more materials can be combined in a manner to achieve the desired optical characteristic. In addition to solids, the exemplary ICE 100 may also contain liquids and/or gases, optionally in combination with solids, in order to produce a desired optical characteristic. In the case of gases and liquids, the ICE 100 can contain a corresponding vessel (not shown), which houses the gases or liquids. Exemplary variations of the ICE 100 may also include holographic optical elements, gratings, piezoelectric, light pipe, and/or acousto-optic elements, for example, that can create transmission, reflection, and/or absorptive properties of interest.

The multiple layers 102, 104 may exhibit different refractive indices. By properly selecting the materials of the layers 102, 104 and their relative thickness and spacing, the ICE 100 may be configured to selectively pass/reflect/refract predetermined fractions of electromagnetic radiation at different wavelengths. Each wavelength is given a predetermined weighting or loading factor. The thickness and spacing of the layers 102, 104 may be determined using a variety of approximation methods from the spectrum of the characteristic or analyte of interest. These methods may include inverse Fourier transform (IFT) of the optical transmission spectrum and structuring the ICE 100 as the physical representation of the IFT. The approximations convert the IFT into a structure based on known materials with constant refractive indices.

The weightings that the layers 102, 104 of the ICE 100 apply at each wavelength may be set to the regression weightings described with respect to a known equation, data, or spectral signature. When electromagnetic radiation interacts with a substance, unique physical and chemical information about the substance may be encoded in the electromagnetic radiation that is reflected from, transmitted through, or radiated from the substance. This information is often referred to as the spectral "fingerprint" of the substance. The ICE 100 may be configured to perform the dot product of the received electromagnetic radiation and the wavelength dependent transmission function of the ICE 100. The wavelength dependent transmission function of the ICE is dependent on the layer material refractive index, the number of layers 102, 104 and thickness of each layer 102, 104. The ICE 100 transmission function is then analogous to a desired regression vector derived from the solution to a linear multivariate problem targeting a specific component of the substance being analyzed. As a result, the output light intensity of the ICE 100 is related to the characteristic or analyte of interest of the substance.

Optical computing devices employing the ICE 100 may be capable of extracting the information of the spectral fingerprint of multiple characteristics or analytes within a substance and converting that information into a detectable output regarding the overall properties of the substance. That is, through suitable configurations of the optical computing devices, electromagnetic radiation associated with characteristics or analytes of interest in a substance can be separated from electromagnetic radiation associated with all other components of the substance in order to estimate the properties of the substance in real-time or near real-time.

Prior to field use, each ICE must be calibrated such that it is able to operate effectively upon being exposed to extreme temperatures and pressures commonly found in downhole environments. If it is not properly calibrated, the resulting transmission functions derived from each ICE may provide well operators with inaccurate measurements or results upon being subjected to the extreme temperatures and pressures.

Figure 2:
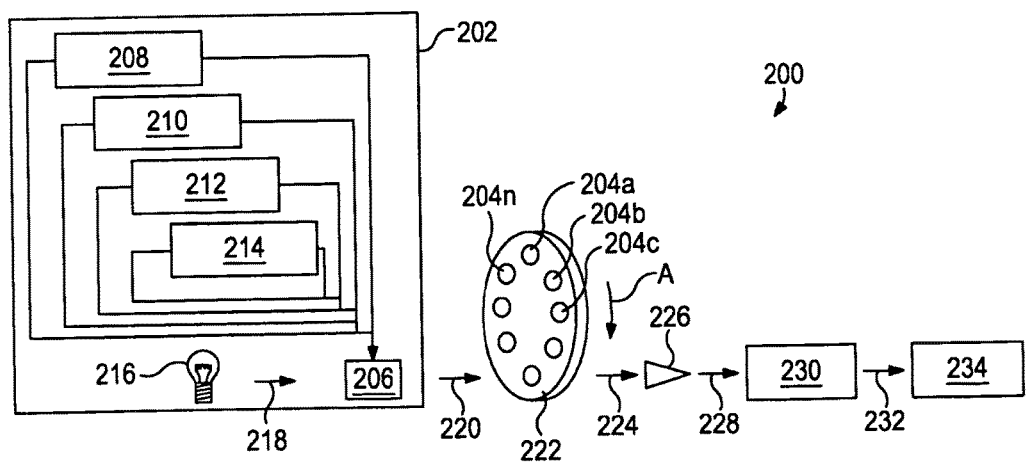
FIG. 2 illustrates a calibration system used to calibrate integrated computational elements.

Referring to FIG. 2, illustrated is a calibration system 200 that may be used to calibrate one or more ICE. As illustrated, the system 200 may include a measurement system 202 in optical communication with one or more ICE 204 (shown as 204a, 204b, 204c, . . . 204n, hereinafter collectively referred to as "ICEs 204") that are to be calibrated. Each of ICEs 204 may be somewhat similar to the ICE 100 of FIG. 1, and therefore will not be described again in detail. The measurement system 202 may be configured to circulate one or more calibration fluids through an optic cell 206 over widely varying calibration conditions of temperature, pressure, density, chemical concentration (i.e., GOR), etc., such that optical transmission and/or reflection measurements of each calibration fluid in conjunction with each of ICEs 204 may be made at such conditions.

As used herein, the term "measurement system" (as in measurement system 202) refers to any type of apparatus or instrument capable of circulating one or more fluids, varying the conditions of such fluids, and measuring the optical properties of such fluids at varying pressures, temperatures, and volumes while in controlled or non-controlled conditions. In some embodiments, the measurement system 202 may be an optical pressure-volume-temperature (PVT) instrument, generally known to those skilled in the art. In other embodiments, however, the measurement system 202 may encompass a cuvette, or the like. For the purposes of this disclosure, the measurement system 202 is shown and described generally as a PVT instrument and therefore the terms "measurement system 202" and "PVT instrument 202" are used interchangeably herein. Such interchangeability of terms, however, is not meant to limit the scope of the disclosure since those skilled in the art will readily appreciate that other types of measurement devices may equally be employed to generate data for the design and calibration of the ICEs 204.

The calibration fluids circulated in the PVT instrument 202 may include representative fluids that each of ICEs 204 may be expected to encounter in field use. Accordingly, the system 200 may be configured to calibrate each of ICEs 204 to the particular chemical compositions found in each calibration fluid at varying calibration conditions. In some embodiments, for example, the calibration fluids are samples of downhole reservoir fluids and otherwise fluids that contain representative spectroscopic absorptions of components commonly found in fluids downhole. The calibration fluids for predictive model development also require necessary diversity to sufficiently cover the dynamic range of the chemical or physical property of interest. The calibration fluids for asphaltene prediction, for example, may include non-asphaltene water, low-asphaltene light oil, high asphaltene heavy oil and other fluid samples such as live oil condensates and natural liquid gas to characterize the property variation.

Some calibration fluids are selected as reference fluids and used in both PVT system and sensor manufacturing laboratories to serve the need of detector output re-scaling or instrument standardization. In at least one embodiment, the reference fluids may include six representative fluids that are easy to operate for manufacturing calibration; namely, dodecane, nitrogen, water, toluene, 1-5 pentanediol and a typical medium oil of abundance. In other embodiments, other representative calibration fluids may be circulated in the PVT instrument 202, depending on the types of fluids the ICEs 204 are likely to encounter in use. Moreover, those skilled in the art will readily appreciate that more or less than six (or different) calibration fluids may be used in the PVT instrument 202 to calibrate the ICEs 204, and will depend primarily on the need for quality prediction and cost constraints. In some embodiments, one or more of the calibration fluids may be a liquid. In other embodiments, however, one or more of the calibration fluids may be a gas, without departing from the scope of the disclosure.

The PVT instrument 202 may be configured to vary each calibration fluid over several set points spanning the varying calibration conditions mentioned above in order to facilitate the calibration of each of ICEs 204. To accomplish this, as illustrated, the PVT instrument 202 may include a liquid charging system 208, a gas charging system 210, a temperature control system 212, and a pressure control system 214.

The calibration fluids are generally "dead" fluids (e.g., laboratory samples from which most of the volatiles have escaped), and the liquid and gas charging systems 208, 210 may be configured to charge the calibration fluids as they circulate in order to simulate "live" fluids, or fluids that will typically be found in a downhole environment. In some embodiments, the liquid charging system 208 may inject another fluid (either dead or live) into the circulating calibration fluids in order to introduce fluid varying perturbations such that calibrating the ICEs 204 will incorporate all the expected compounds found in the particular calibration fluid. In one or more embodiments, for example, a calibration fluid may be charged or otherwise diluted with toluene as injected by the liquid charging system 208.

The gas charging system 210 may be configured to inject a known gas into the circulating calibration fluids. Similar to the liquid charging system 208, this may be done to perturb the calibration fluid, but this may also be done to re-inject volatiles back into the "dead" calibration fluid and thereby more accurately simulate fluids that each of ICEs 204 will encounter downhole. Injecting gases into the calibration fluid also serves to vary or otherwise regulate the GOR of each calibration fluid to differing degrees. Exemplary gases that may be injected into the calibration fluids include, but are not limited to, $N_2$, $CO_2$, $H_2S$, methane, propane, ethane, butane, combinations thereof, and the like. Each of these compounds are low-boiling gases that typically escape sample fluids during the sampling process. As can be appreciated, the amount of gas injected into the calibration fluid via the gas charging system 210 may vary depending on what GOR is to be simulated in the PVT instrument 202 in order to meet a particular calibration condition or GOR set point.

The temperature control system 212 may be configured to vary the temperature of the calibration fluid in order to simulate several temperature set points that the ICEs 204 may encounter downhole. To accomplish this, the temperature control system 212 may include or otherwise encompass one or more of an oven, a heat exchanger, a heating element, or any device configured to regulate the temperature of a fluid. The number of temperature set points to which the temperature control system 212 will heat each calibration fluid will vary, depending primarily on time and cost constraints. In at least one embodiment, the temperature control system 212 may be configured to heat each calibration fluid to temperature set points of 150° F., 200° F., 250° F., 300° F., and one or more temperature set points falling therebetween. Those skilled in the art, however, will readily recognize that more or less temperature set points than listed above may equally be used, without departing from the scope of the disclosure.

The pressure control system 214 may be configured to vary the pressure of the calibration fluid in order to simulate several pressure set points that the ICEs 204 may encounter downhole. To accomplish this, the pressure control system 214 may include or otherwise encompass one or more compressors or pumps that regulate the pressure of the calibration fluid. Similar to the temperature control system 212, the number of pressure set points to which the pressure control system 214 will pressurize each calibration fluid will vary, depending primarily on time and cost constraints. In at least one embodiment, the pressure control system 214 may be configured to pressurize each calibration fluid to pressure set points of 3000 psi, 6000 psi, 9000 psi, 12,000 psi, and one or more pressure set points falling there between. Those skilled in the art, however, will again readily recognize that more or less pressure set points than listed above may equally be used, without departing from the scope of the disclosure.

The optic cell 206 is fluidly coupled to each of the systems 208, 210, 212, and 214 such that each calibration fluid is able to flow therethrough and recirculate back to each of the systems 208, 210, 212, and 214 in a continuous, closed-loop circuit. As will be appreciated, several valves, conduits, and other known fluid coupling devices are not specifically shown in FIG. 2 but are nonetheless included in the PVT instrument 202 in order to facilitate the closed-loop circuit. The optic cell 206 may define an internal fluid flow path fluidly coupled to each system 208, 210, 212, and 214 and extending between two transparent windows made of, for example, glass, plastic, semi-conductors, crystalline materials, polycrystalline materials, hot or cold-pressed powders, combinations thereof, or the like. During circulation, the calibration fluids flow through the flow path and a light source 216 may be configured to emit electromagnetic radiation 218 that passes through the transparent windows of the optic cell 206 and the calibration fluid flowing therethrough. The light source 216 may be, for example, a light bulb, a light emitting diode (LED), a laser, a blackbody, a photonic crystal, an X-Ray source, combinations thereof, or the like.

As the electromagnetic radiation 218 passes through the optic cell 206 it optically interacts with the calibration fluid and generates sample interacted light 220. The sample interacted light 220 may include spectral data for the particular calibration fluid circulating through the PVT instrument 202 at the given calibration conditions. The sample interacted light 220 may be directed toward the ICEs 204 which, as illustrated, may be arranged or otherwise disposed within a filter wheel 222 configured to rotate in the direction A. The ICEs 204 may be radially disposed about the periphery of the filter wheel 222 and otherwise circumferentially-spaced from each other for rotation therewith. During operation of the system 200, the filter wheel 222 may be rotated at a predetermined frequency such that the individual ICEs 204 may each be exposed to or otherwise optically interact with the sample interacted light 220 for a brief period of time. Upon optically interacting with the sample interacted light 220, each of ICEs 204 may sequentially produce optically interacted light 224 that is conveyed or otherwise directed to a detector 226 in sequence.

The detector 226 may be any device capable of detecting electromagnetic radiation, and may be generally characterized as an optical transducer. The detector 226 may be, for example, a thermal detector, such as a thermopile or photoacoustic detector, a semiconductor detector, a piezo-electric detector, a charge coupled device (CCD) detector, a video or array detector, a split detector, a photon detector (such as a photomultiplier tube), photodiodes, combinations thereof, or the like, or another detector known to those skilled in the art. Upon receiving individually-detected beams of optically interacted light 224 from each of ICEs 204, the detector 226 may generate or otherwise convey corresponding response signals 228 to a data acquisition system 230.

The data acquisition system 230 may be configured to time multiplex each response signal 228 received from the detector 226 corresponding to each of ICEs 204. A corresponding set of resulting output signals 232 is subsequently generated and conveyed to a data analysis system 234 for processing. Each resulting output signal 232 may be graphically represented as a regression vector dot product corresponding to the optical interaction between each of ICEs 204 and the calibration fluid circulating in the PVT instrument 202 at the particular set point calibration conditions.

Output signal 232 may be input into the data analysis system 234 to determine a corresponding gain and offset that may be applied to each regression vector dot product at such calibration conditions. By applying the gain and offset directly to the ICEs 204, a direct calibration of the ICEs 204 may result in view of real downhole fluids. In other embodiments, however, the ICEs 204 may be calibrated against the representative calibration fluids and the signals 232 are converted to archived, real downhole signals, thereby resulting in a "master ICE sensor." More particularly, the data analysis system 234 may include or otherwise employ a calibration coefficient matrix that facilitates a comparison of each resulting output signal 232 with archived regression vector dot products for the calibration fluids. The differences between the regression vector dot products generated by each of ICEs 204 at the calibration conditions of the PVT instrument 202 and the archived regression vector dot products of the calibration fluids provide a gain and offset that may be applied to each corresponding ICEs 204, thereby calibrating the ICEs 204 for use in a downhole environment exhibiting substantially similar calibration conditions. Alternatively, each of the calibration signals from the ICEs 204 may be transferred to fluid spectral data.

The foregoing process, for example to calibrate for GOR, may be characterized as a single laboratory run undertaken at a first calibration condition encompassing a given temperature, a given pressure, and a given GOR for a single calibration fluid. In order to fully calibrate a set of ICEs 204 for use in a downhole tool, several laboratory runs must be undertaken at several different calibration conditions for each calibration fluid. In other words, a set of ICEs 204 for a particular downhole tool must be calibrated against each calibration fluid at several varying temperature set points, pressure set points, and/or GOR set points. As can be appreciated, the total number of laboratory runs can grow quickly according to the following expression:

$$\text{Total \# of Runs} = (N_{fluid} \times N_X \times N_P \times N_T) \times N_{tool} \qquad \text{Equation (1)}$$

where $N_{fluid}$ is the total number of calibration fluids used for calibration; $N_P$ is the total number of pressure set points to cover the field operational pressure range; $N_T$ is the total number of temperature points to cover the field operational range; $N_{tool}$ is the total number of downhole tools to be calibrated, each with a different set of ICEs 204; and $N_X$ is a desired fluid parameter (i.e., the concentration of saturates or aromatics in a reservoir fluid), and is representative here of the total number of GOR set points for each calibration fluid.

Notably, each time a calibration condition or set point is altered, there is a considerable waiting period before the PVT instrument 202 reaches the new equilibrium or steady state. For example, each time a temperature set point is changed, the system 200 will be on hold until the calibration fluid in the PVT instrument 202 equilibrates to the new temperature. Similarly, each time a pressure set point is changed, the system 200 will be on hold until the calibration fluid in the PVT instrument 202 equilibrates to the new pressure set point. The same follows for changes to GOR in the calibration fluid. As a result, the foregoing calibration process can be a time-consuming and costly undertaking. In some instances, it may take up to four weeks to calibrate one set of ICEs 204 for a single tool.

According to the present invention, the time to calibrate a set of ICEs 204 may be dramatically reduced by using a spectrometer to collect complete spectral data for each calibration fluid at each calibration condition (i.e., each temperature, pressure, and GOR set point). Once this spectral data is collected, it may be used to program a virtual light source operable to simulate the spectral responses of each calibration fluid at each predetermined calibration condition. As a result, the complex and time-consuming PVT instrument 202 would no longer be necessary for future calibration operations. Instead, the PVT instrument 202 may be generally replaced with the virtual light source containing all the required spectral responses for all calibration fluids at all desired temperature, pressure, and GOR set points.

Figure 3:
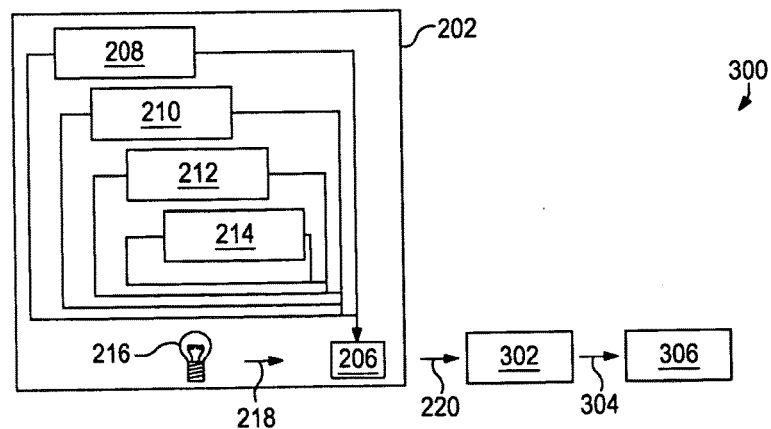
FIG. 3 illustrates a modified calibration system, according to one or more embodiments.

Referring now to FIG. 3, illustrated is a modified calibration system 300, according to one or more embodiments. The modified calibration system 300 may be a modified version of the system 200 shown in FIG. 3 and therefore may be best understood with reference thereto, where like numerals represent like components that will not be described again in detail. As illustrated in FIG. 3, the calibration system 300 may be modified by replacing the filter wheel 222 of FIG. 2 with a spectrometer 302 such that the spectrometer 302 is arranged to receive and process the sample interacted light 220 derived from the optic cell 206. The spectrometer 302 may be any device known in the art that is capable of detecting and measuring electromagnetic radiation. In some embodiments, for example, the spectrometer 302 may be a Fourier transform infrared spectrometer (FTIR). In other embodiments, however, the spectrometer 302 may be a grating monochromator.

Figure 4A:
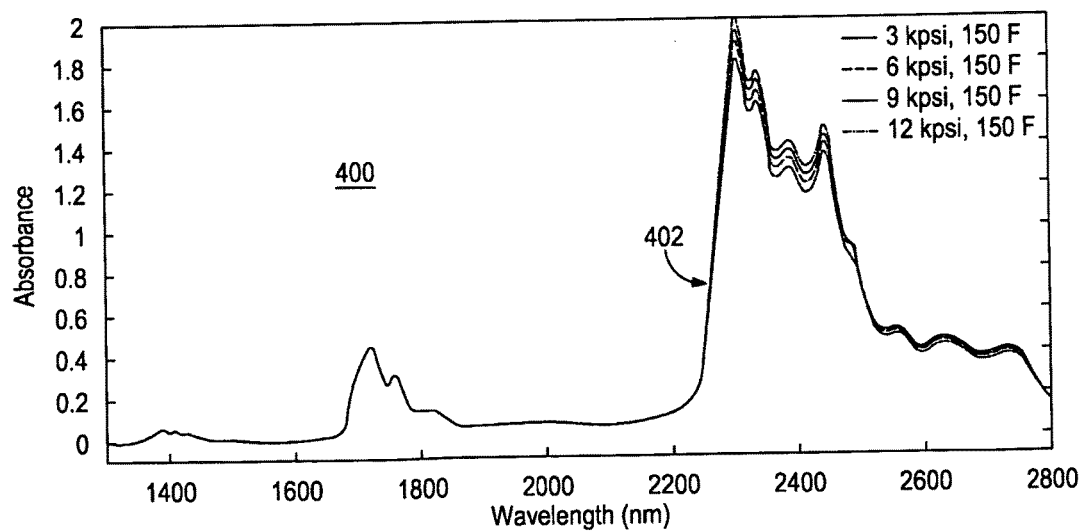
FIG. 4A is a plot depicting spectra corresponding to isothermal absorbance of hexane as plotted against wavelength.
Figure 4B:
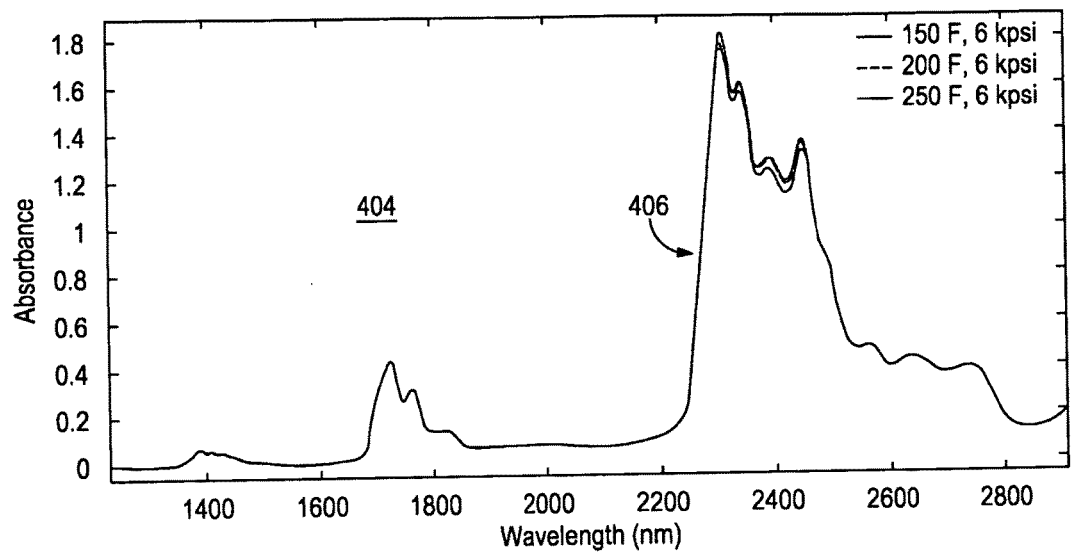
FIG. 4B is a plot depicting spectra corresponding to isobaric absorbance of hexane as plotted against wavelength.

In operation, the spectrometer 302 may be configured to receive and measure the sample interacted light 220, thereby obtaining and otherwise generating the complete spectral data for each calibration fluid circulated in the PVT instrument 202 at each desired calibration condition. Examples of such generated spectra are depicted in FIGS. 4A and 4B, where the isothermal and isobaric absorbance of an exemplary calibration fluid at exemplary calibration conditions is plotted against wavelength. More specifically, FIG. 4A is a first plot 400 that depicts spectra 402 corresponding to isothermal absorbance at 150° F. of hexane as plotted against wavelength, and FIG. 4B is a second plot 404 that depicts spectra 406 corresponding to isobaric absorbance at 6000 psi of hexane as plotted against wavelength.

As will be appreciated, numerous spectra similar to the spectra 402 and 406 of FIGS. 4A and 4B, respectively, may be generated by the spectrometer 302 for each calibration fluid circulated in the PVT instrument 202 at each desired calibration condition. Once the required spectra of the optically interacted light 224 are captured by the spectrometer 302, spectral signals 304 corresponding to each collected spectra may be conveyed to and otherwise programmed into a virtual light source 306. More particularly, each spectral signal 304 may be presented as intensity as a function of wavelength (i.e., transmittance or absorbance). This intensity is converted to a signal that is able to be conveyed to and otherwise received by the virtual light source 306. In at least one embodiment, this may be done as a digitized table of wavelength (or frequency) and intensity, and the virtual light source 306 may be capable of reproducing the digitized table. In other embodiments, this may be done as an electrical signal versus time, which is then translated to intensity vs. wavelength.

In operation, the virtual light source 306 may be configured to provide programmable spectral output or illumination and otherwise simulate the spectral response of a calibration fluid under predetermined calibration conditions. In some embodiments, the virtual light source 306 may be an agile light source (ALS), such as the OL 490 Agile Light Source commercially-available through Cambridge Analytical Instruments of London, United Kingdom. In other embodiments, the virtual light source 306 may be the Firefly™-IR commercially-available through M Squared Lasers, Ltd. of Glasgow, Scotland.

Figure 5:
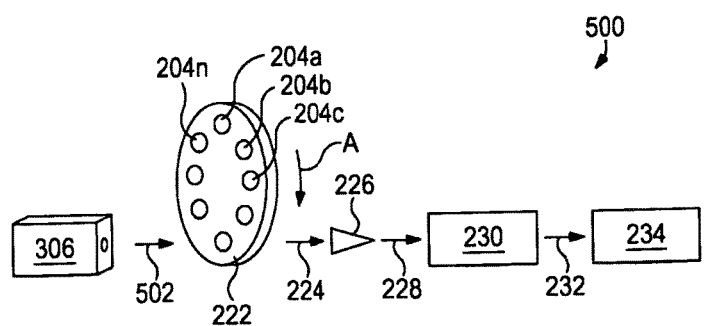
FIG. 5 illustrates an improved calibration system used to calibrate integrated computational elements, according to one or more embodiments.

Referring now to FIG. 5, with continued reference to FIGS. 2 and 3, illustrated is an improved calibration system 500, according to one or more embodiments. Similar to the calibration system 200 of FIG. 2, the improved calibration system 500 may include the filter wheel 222 with one or more ICEs 204 radially disposed therein for rotation therewith, the detector 226, the data acquisition system 230, and the data analysis system 234. Unlike the system 200 of FIG. 2, however, the improved calibration system 500 may replace the PVT instrument 202 with the virtual light source 306 described above with reference to FIG. 3.

The virtual light source 306 may be pre-programmed with each spectrum derived from each calibration fluid circulating in the PVT instrument 202 at each desired calibration condition. As mentioned above with reference to FIG. 3, this may be accomplished by capturing the required spectra of the optically interacted light 220 using the spectrometer 302, and programming the spectral signals 304 compiled by the spectrometer 302 into the virtual light source 306. Once properly programmed with all the spectral signals 304, the virtual light source 306 may operate by conveying simulated fluid spectra 502 to the ICEs 204 rotating on the filter wheel 222. The simulated fluid spectra 502 may instantaneously replicate the spectral responses of each calibration fluid at each predetermined calibration condition. As a result, the complex and time-consuming PVT instrument 202 would no longer be necessary for future calibration operations. Instead, the PVT instrument 202 may be generally replaced with the virtual light source 306 containing all the required spectral responses for all calibration fluids at all desired temperature, pressure, and GOR set points.

Upon optically interacting with the simulated fluid spectra 502, each ICEs 204 may sequentially produce optically interacted light 224 that may be received by the detector 226 in sequence as the filter wheel 222 rotates, for example, in direction A. Upon receiving the individually-detected beams of optically interacted light 224 from each of ICEs 204, the detector 226 may generate corresponding response signals 228 to the data acquisition system 230 which time multiplexes each response signal 228 received from the detector 226 corresponding to each of ICEs 204. The resulting output signals 232 are then generated and conveyed to the data analysis system 234 for processing and calibration of the ICEs 204, as generally described above.

Once the ICEs 204 are properly calibrated, a new set of ICE (not shown) for a new downhole tool may be introduced into the calibration system 500 and the foregoing process may be repeated until the new set of ICE is also properly calibrated against the calibration fluids at each of the calibration conditions programmed into the virtual light source 306. As will be appreciated, this process may be repeated for as many sets of ICE pertaining to corresponding number of downhole tools as needed.

Those skilled in the art will readily appreciate the several advantages that the disclosed systems and methods may provide. For instance, using the virtual light source 306 may greatly shorten the time and effort for calibration since only a single set of complete laboratory data is required to program the virtual light source. Any subsequent calibrations can then be carried out virtually without the need to equilibrate the PVT instrument 202 following any change in calibration conditions. As will be appreciated, this may equate to a substantial savings in capital expenditures since the PVT instrument 202 is only needed to be run once to obtain the needed data. As a result, there may be a substantial reduction in the need to maintain and repair the PVT instrument 202.

Moreover, the systems and methods described herein may provide flexibility for future sensor ICE calibration. For example, as additional spectra from additional calibration fluids at varying calibration conditions are collected and stored, the available database for the virtual light source 306 grows. As a result, it may not be necessary to re-measure the same calibration fluids over similar calibration conditions already measured since such measurements were already undertaken and stored for future reference.

Additional advantages provided by the presently disclosed systems and methods include a reduction of waste materials since sets of calibration fluids are no longer needed to be run and disposed of following calibration. Also, the systems and methods improve health and safety since there is significantly less (if any) handling of potentially harmful or explosive chemicals at elevated temperatures and pressures for the calibration. Lastly, the presently disclosed systems and methods improve standardization of the ICE sensors since they all can be calibrated to the identical simulated spectra.

Additionally, once the required data is obtained and programmed into the virtual light source 306, the methods disclosed herein may be easily adaptable for field calibration where a PVT instrument is not available or otherwise tenable. For instance, in at least one embodiment, the virtual light source 306 may be sent downhole with a downhole tool such that a set of ICE may be calibrated and otherwise re-calibrated while the downhole tool operates. This may further prove advantageous in the event a downhole light source needs to be replaced and or allow well operators to use a variable light source when encountering, for example, fairly opaque fluids to be monitored.

The computers and signal processors described herein may include computer hardware used to implement the various computations and operations required to accurately detect a desired analyte of interest. The computer hardware may include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein, including the general movement of the polarizers between x and y polarization angles, data collection from the various detectors, and normalizing the detected signals. Thus, the present embodiments are not limited to any specific combination of hardware and/or software.

As used herein, a machine-readable medium refers to any non-transitory medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A method of calibrating an output signal from an integrated computational element (ICE), comprising:
   configuring a virtual light source to emit a radiation that replicates an absorbance feature or a transmittance feature of a calibration fluid at multiple calibration conditions that comprise one of a plurality of temperatures, a plurality of pressures, or a plurality of fluid compositions;
   conveying the radiation to the ICE and generating an optically interacted light;
   receiving the optically interacted light with a detector that generates a response signal corresponding to the optically interacted light;
   receiving the response signal with a data acquisition system to generate the output signal;
   determining a gain and an offset to be applied to an output signal from the optically interacted light by comparing the output signal with archived regression vectors of known reference fluids; and
   storing the gain and the offset in a non-transitory, computer readable medium.

2. The method of claim 1, wherein configuring the virtual light source to emit a radiation that replicates an absorbance feature of a calibration fluid comprises conveying spectral signals generated in a spectrometer to the virtual light source, the spectral signals corresponding to collected spectra derived from the calibration fluid circulating in a measurement system at the calibration conditions.

3. The method of claim 1, further comprising rotating the ICE on a filter wheel, the ICE being arranged radially about a periphery of the filter wheel.

4. The method of claim 1, wherein the calibration fluid comprises at least a first calibration fluid, and wherein to derive the absorbance feature or the transmittance feature from the calibration fluid comprises:
   circulating the first calibration fluid through an optic cell;
   altering at least one of a temperature, a pressure, and a gas-oil-ratio of the first calibration fluid to obtain a first calibration condition of the calibration conditions;
   equilibrating a measurement system to the first calibration condition;
   optically interacting electromagnetic radiation with the first calibration fluid as it flows through the optic cell and thereby generating a first sample interacted light of a sample interacted light; and
   conveying the first sample interacted light to a spectrometer, the first sample interacted light comprising spectral data derived from the first calibration fluid at the first calibration condition.

5. The method of claim 1, further comprising:
   replacing the ICE with an additional ICE;
   conveying the radiation to the additional ICE and thereby generating corresponding additional beam of optically interacted light; and
   calibrating the additional ICE based on the corresponding additional beam of optically interacted light.

6. The method of claim 5, further comprising circulating the first calibration fluid through at least one of a liquid charging system, a gas charging system, a temperature control system, and a pressure control system in order to achieve the first calibration condition, the optic cell being fluidly coupled to the at least one of the liquid charging system, the gas charging system, the temperature control system, and the pressure control system.

7. The method of claim 5, further comprising:
   altering at least one of the temperature, the pressure, and the gas-oil-ratio of the first calibration fluid to obtain a second calibration condition of the calibration conditions;
   equilibrating the measurement system to the second calibration condition;

optically interacting electromagnetic radiation with the first calibration fluid as it flows through the optic cell and thereby generating a second sample interacted light of the sample interacted light; and conveying the second sample interacted light to the spectrometer, the second sample interacted light comprising spectral data derived from the first calibration fluid at the second calibration condition.

8. The method of claim 7, wherein the calibration fluid further comprises a second calibration fluid, the method further comprising:

circulating the second calibration fluid through the optic cell;

altering at least one of a temperature, a pressure, and a gas-oil-ratio of the second calibration fluid to obtain a third calibration condition of the calibration conditions;

equilibrating the measurement system to the third calibration condition;

optically interacting electromagnetic radiation with the second calibration fluid as it flows through the optic cell and thereby generating a third sample interacted light of the sample interacted light; and conveying the third sample interacted light to the spectrometer, the third sample interacted light comprising spectral data derived from the second calibration fluid at the third calibration condition.

9. The method of claim 8, further comprising:

altering at least one of the temperature, the pressure, and the gas-oil-ratio of the second calibration fluid to obtain a fourth calibration condition of the calibration conditions;

equilibrating the measurement system to the fourth calibration condition;

optically interacting electromagnetic radiation with the second calibration fluid as it flows through the optic cell and thereby generating a fourth sample interacted light of the sample interacted light; and conveying the fourth sample interacted light to the spectrometer, the fourth sample interacted light comprising spectral data derived from the second calibration fluid at the fourth calibration condition.

10. A system, comprising:

a virtual light source configured to emit a radiation that replicates an absorbance feature or a transmittance feature of a calibration fluid circulating in a measurement system at one or more calibration conditions, wherein the one or more calibration conditions comprises one of a plurality of temperatures, a plurality of pressures, or a plurality of fluid compositions;

an integrated computational element (ICE) arranged to receive the radiation from the virtual light source, the ICE being configured to generate an optically interacted light;

a detector arranged to receive the optically interacted light and generate a response signal corresponding to the optically interacted light;

a data acquisition system arranged to receive the response signal and generate an output signal corresponding to the ICE; and a data analysis system arranged to receive the output signal and configured to determine a corresponding gain and offset to be applied to the output signal corresponding to the ICE by comparing the output signal with archived regression vectors of the calibration fluid.

11. The system of claim 10, wherein the absorbance feature derived from a light interacted with the calibration fluid is collected with a Fourier transform infrared spectrometer.

12. The system of claim 10, wherein the virtual light source is a programmable agile light source.

13. The system of claim 10, wherein the ICE is arranged radially about a periphery of a filter wheel, the filter wheel comprising a second ICE.

14. The system of claim 10, wherein the virtual light source is installed within a downhole tool and conveyed downhole such that the corresponding gain and offset are applied to the output signal corresponding to the ICE when the ICE is downhole.

15. The system of claim 10, wherein the one or more calibration conditions comprise a pressure condition of the calibration fluid, a volume condition of the calibration fluid, and a temperature condition of the calibration fluid.

16. The system of claim 10, wherein the measurement system comprises:

a liquid charging system;

a gas charging system;

a temperature control system;

a pressure control system;

an optic cell having the calibration fluid flowing therethrough and being fluidly coupled to the liquid charging system, the gas charging system, the temperature control system, and the pressure control system; and a light source in optical communication with the optic cell and being configured to emit an electromagnetic radiation that optically interacts with the calibration fluid to generate a sample interacted light.

17. The system of claim 16, wherein at least one of a temperature, a pressure, and a gas-oil-ratio of a first calibration fluid is altered in order to obtain a first calibration condition of the one or more calibration conditions, and wherein the electromagnetic radiation interacts optically with the first calibration fluid to generate a first sample interacted light of the sample interacted light, the first sample interacted light being conveyed to a spectrometer and comprising spectral data derived from the first calibration fluid at the first calibration condition.

18. The system of claim 17, wherein at least one of the temperature, the pressure, and the gas-oil-ratio of the first calibration fluid is altered in order to obtain a second calibration condition of the one or more calibration conditions, and wherein the electromagnetic radiation interacts optically with the first calibration fluid to generate a second sample interacted light of the sample interacted light, the second sample interacted light being conveyed to the spectrometer and comprising spectral data derived from the first calibration fluid at the second calibration condition.

19. The system of claim 18, wherein a second calibration fluid is circulated through the optic cell and at least one of a temperature, a pressure, and a gas-oil-ratio of the second calibration fluid is altered in order to obtain a third calibration condition of the one or more calibration conditions, and wherein the electromagnetic radiation interacts optically with the second calibration fluid to generate a third sample interacted light of the sample interacted light, the third sample interacted light being conveyed to the spectrometer and comprising spectral data derived from the second calibration fluid at the third calibration condition.

20. The system of claim 19, wherein at least one of the temperature, the pressure, and the gas-oil-ratio of the second calibration fluid is altered in order to obtain a fourth calibration condition of the one or more calibration conditions, and wherein the electromagnetic radiation interacts optically with the second calibration fluid to generate a fourth sample interacted light of the sample interacted light, the fourth sample interacted light being conveyed to the spectrometer and comprising spectral data derived from the second calibration fluid at the fourth calibration condition.

\* \* \* \* \*